(12) United States Patent
Badura et al.

(10) Patent No.: US 6,509,573 B1
(45) Date of Patent: Jan. 21, 2003

(54) APPARATUS AND METHOD FOR CONTROLLING A RADIATION DEVICE

(75) Inventors: Eugen Badura, Mühltal (DE); Holger Brand, Darmstadt (DE); Hans-Georg Essel, Darmstadt (DE); Thomas Haberer, Frankfurt am Main (DE); Jan Hoffmann, Darmstadt (DE); Wolfgang Ott, Dossenheim (DE); Klaus Poppensieker, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/409,550

(22) Filed: Sep. 30, 1999

(51) Int. Cl.⁷ ................................................. A61N 5/01
(52) U.S. Cl. ...................... 250/492.3; 709/251; 700/1
(58) Field of Search .................. 250/492.3; 709/251; 700/1

(56) References Cited

U.S. PATENT DOCUMENTS

| 4,477,882 A | 10/1984 | Schumacher et al. | 364/900 |
| 5,017,789 A | 5/1991 | Young et al. | 250/396 |
| 5,260,581 A | * 11/1993 | Lesyna et al. | 250/492.3 |

FOREIGN PATENT DOCUMENTS

| DE | 196 33 744 A1 | 8/1996 |
| EP | 0 143 993 | 6/1985 |
| WO | WO 96/25201 | 8/1996 |

OTHER PUBLICATIONS

IBM Technical Disclosure Bulletin, Feb. 1994, vol. 37, No. 2B, pp. 641–644.*
"Systems for Overall Control and Beam Transport of the HIMAX," Jun Mastsu'ura, *Mitsubishi Electric Advance*, Technical Reports, Sep. 1995, pp. 5–7.
"Control System for the Neutron Therapy Facility at Fermilab," Shea et al., *Proceedings of the 1989 IEEE Particle Accelerator Conference*, Fermi National Accelerator Laboratory, FN–512, Mar. 1989, pp. 1–3.
"Magnetic Scanning System for Heavy Ion Therapy," Haberer et al., *Nuclear Instruments & Methods in Physics Research*, Section A, Elsevier Science Publishers B.V., 1993, pp. 296–305.

* cited by examiner

Primary Examiner—Jack Berman
(74) Attorney, Agent, or Firm—Marshall, Gerstein & Borun

(57) ABSTRACT

An arrangement and a method for controlling a radiation device, in particular for heavy ion therapy, are described. The arrangement comprises a chain of circuit modules (11–17), each circuit module (11–17) having a separate communication connection to a preceding circuit module and a separate communication connection to a following circuit module. In the method for controlling the radiation device by means of control modules (11–17) arranged in a chain, each control module (11–17) communicates separately with a preceding control module and separately with a following control module.

17 Claims, 4 Drawing Sheets

APPARATUS AND METHOD FOR CONTROLLING A RADIATION DEVICE

Figure 1:
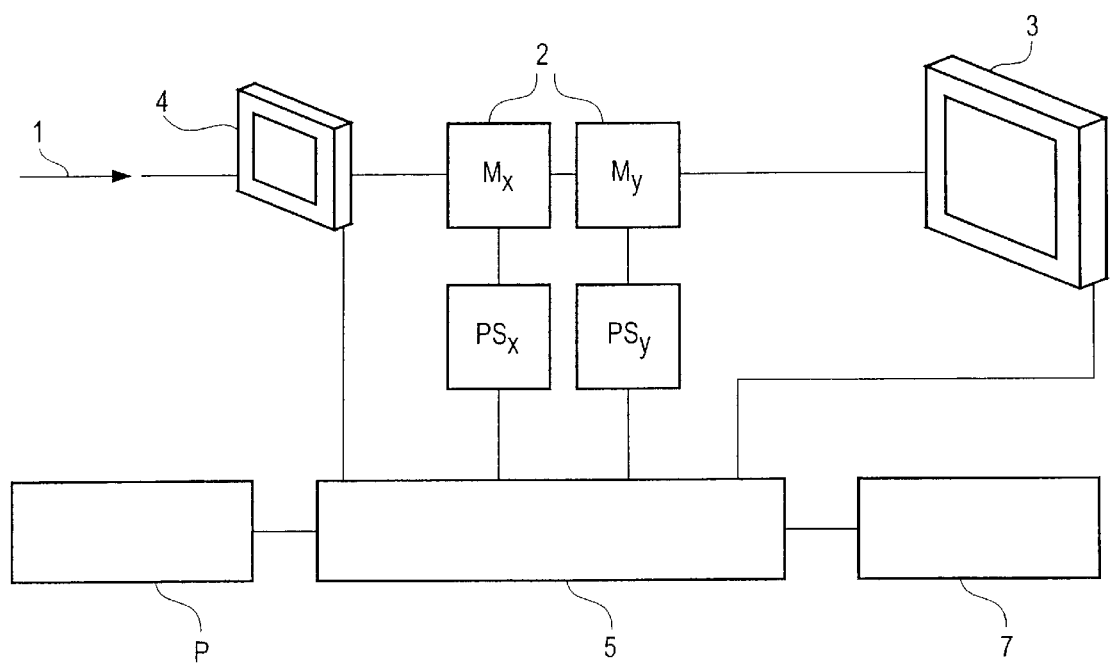

The present invention relates to an arrangement and a method for controlling a radiation device.

Such an arrangement is used in particular in a radiotherapy system for the treatment of tumours. Rays that come into consideration for use are particle rays, such as, for example, protons or heavy ions. In tumour therapy, particle rays offer special physical advantages over electromagnetic rays; for example, they have a so-called "inverted" dose profile, that is, the radiation dose deposited in the target volume—the tumour tissue—increases as the depth of penetration increases and has a sharp peak just before its maximum reach. With electromagnetic rays, on the other hand, the deposited radiation dose decreases as the depth of penetration increases, and a large part of the radiation dose is deposited in healthy tissue in front of and behind the tumour. In addition, particle rays are subject to substantially less deflection as they pass through thick tissue layers, and can be focussed extremely accurately on the tumour using magnetic lenses. Particle rays can therefore in principle be focussed on a target volume more effectively than electromagnetic rays. Moreover, heavy ions, for example, carbon or oxygen ions, additionally have significant biological benefits over protons in the destruction of tumour cells that are especially resistant to radiation.

For exact distribution of the heavy ion radiation dose over the target volume, it is known to proceed in accordance with the so-called raster scan method, used similarly in body-section radiography. A description of this method will be found in an article by Th. Haberer, W. Becher, D. Schardt and D. Kraft entitled "Magnetic scanning system for heavy ion therapy", which appeared in "Nuclear Instruments and Methods in Physics Research" A330 (1993), p. 296–305. Here, the target volume is "separated" into individual slices of identical particle reach. In each slice, a grid pattern of points is defined, for each of which a number of particles to be deposited by the irradiation (radiation dose) is determined. The totality of the points and the particle numbers and particle energies allocated to them, that is, the distribution of the particle numbers over the total target volume, form a radiation plan. Starting with the rearmost slice, the particle ray, deflected by a pair of magnetic deflecting devices, scans each slice raster-fashion. The dose is varied from point to point in each slice, by directing the particle ray onto a point until the desired particle number value in accordance with the irradiation plan is reached.

It is difficult, however, to achieve an exact, reliable and sufficiently rapid control of the radiation device. Note that in the following text the term "control of a device" is used for the control and/or the monitoring of the same.

Up till now it has also been a problem to synchronise the control devices for beam deflection and particle number with one another such that during the course of irradiation they each relate at the same time to the same point in accordance with the irradiation plan. Otherwise, there is a risk that the patient will be harmed by an uncontrolled radiation process.

It is therefore the aim of the invention to produce an arrangement and a method for controlling a radiation device, which ensure an exact, rapid and reliable control of the beam.

According to the invention, the arrangement for controlling a radiation device comprises a chain of circuit modules, each circuit module having a separate communication connection to a preceding circuit module and a separate communication connection to a following circuit module.

In the method according to the invention for controlling a radiation device by means of control modules arranged in a chain, each control module communicates separately with a preceding control module and separately with a following control module.

The arrangement according to the invention and the method according to the invention are associated with a series of advantages. The provision of a separate communication connection to a preceding circuit module and a separate communication connection to a following circuit module allows reliable exchange of data between two circuit modules each time. Moreover, the communication of the other circuit module pairs is independent thereof, resulting in a separation of the data path and hence greater reliability of the arrangement.

According to a preferred exemplary embodiment of the invention, the radiation device can be in the form of a heavy ion radiation device. Using this device, it is possible advantageously to carry out especially precise and effective tumour treatments.

According to a further aspect of the invention, in the arrangement at least one of the circuit modules can have a connection to an external memory facility. It is thus possible for data to be read out and monitored without influencing the operational sequence of the beam control.

According to a further aspect of the invention, in the arrangement all circuit modules can have a common trigger bus. Exact synchronisation of all circuit modules can therefore advantageously be achieved.

Figure 2:
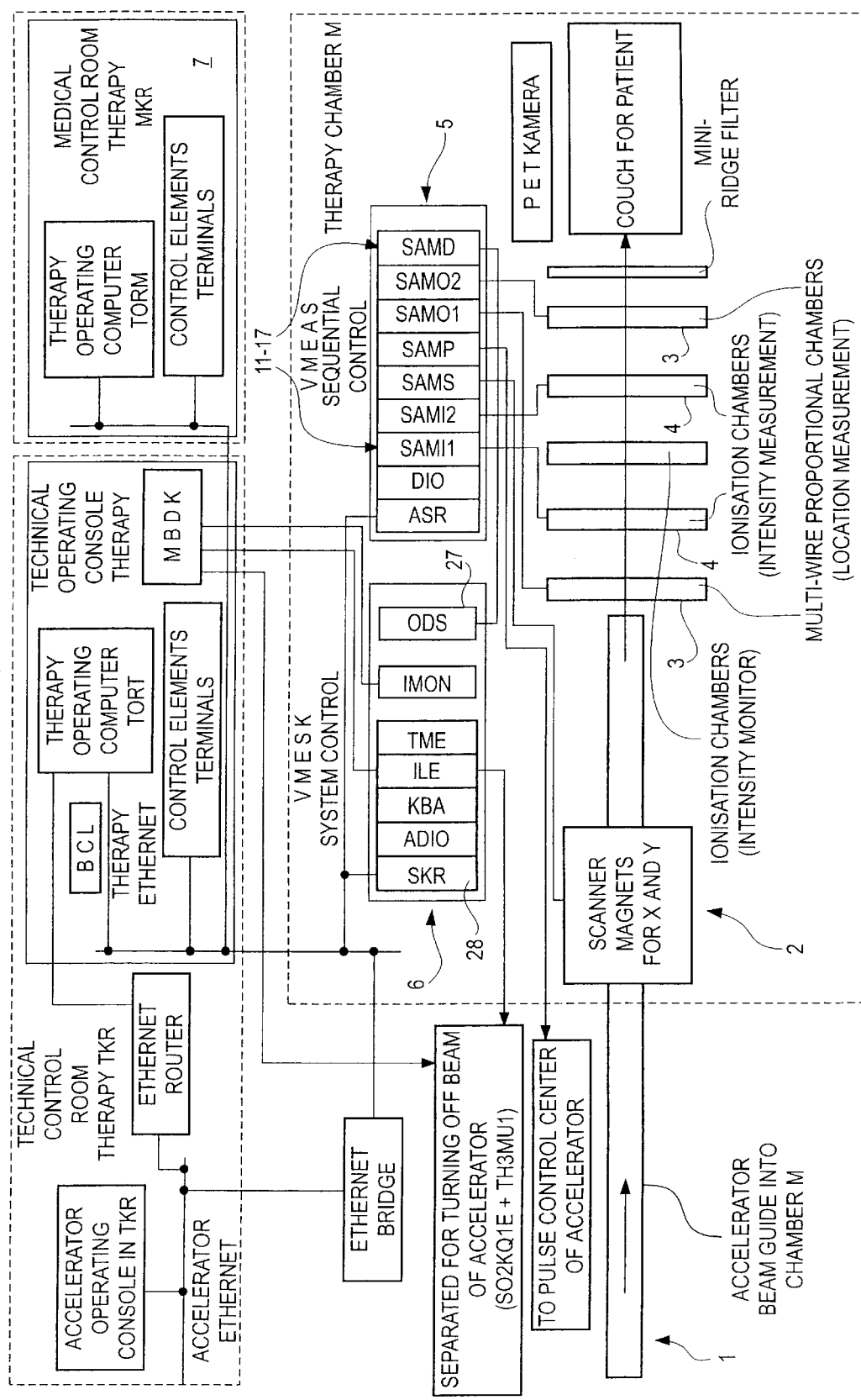
Figure 3:
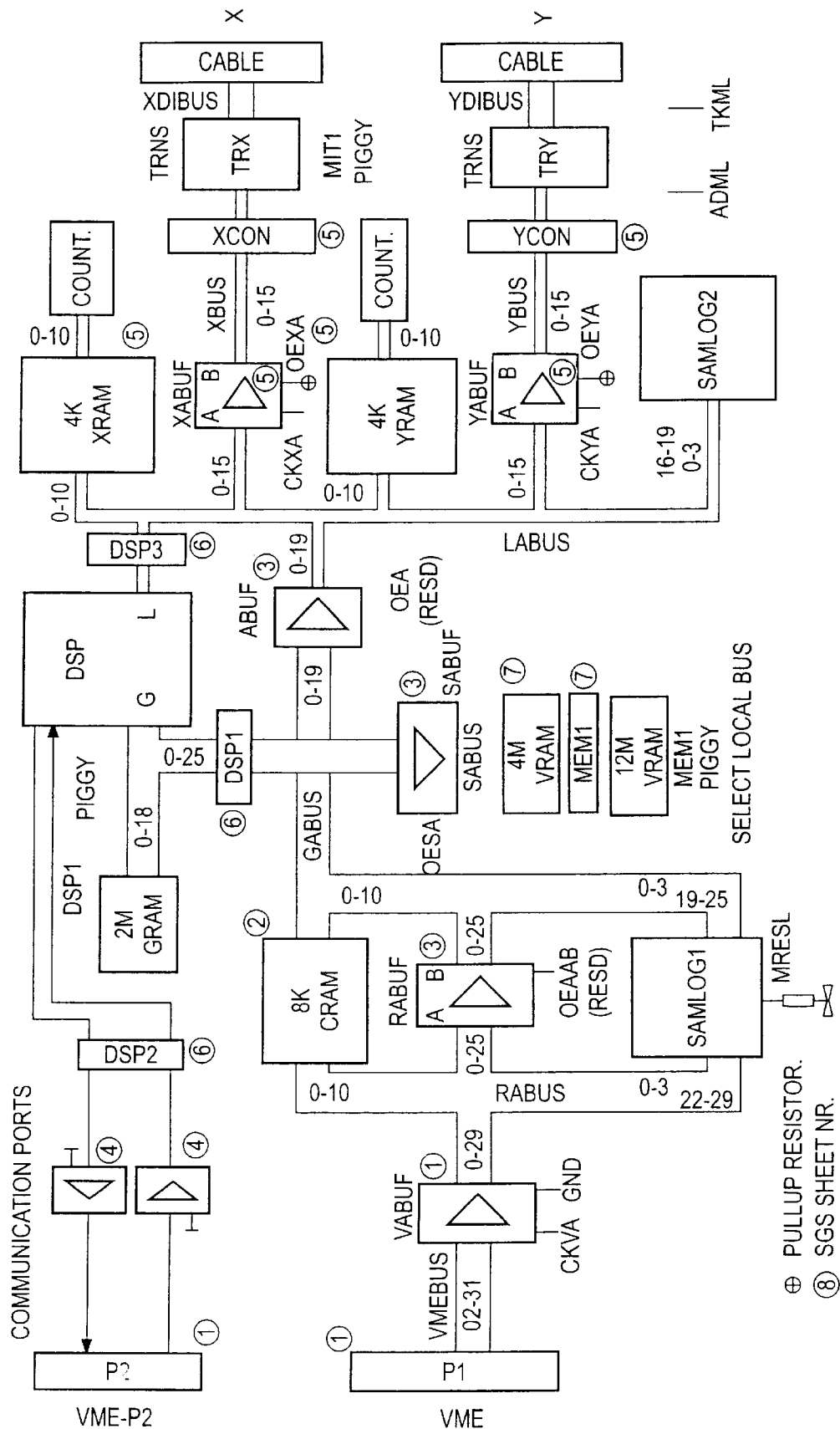
Figure 4:
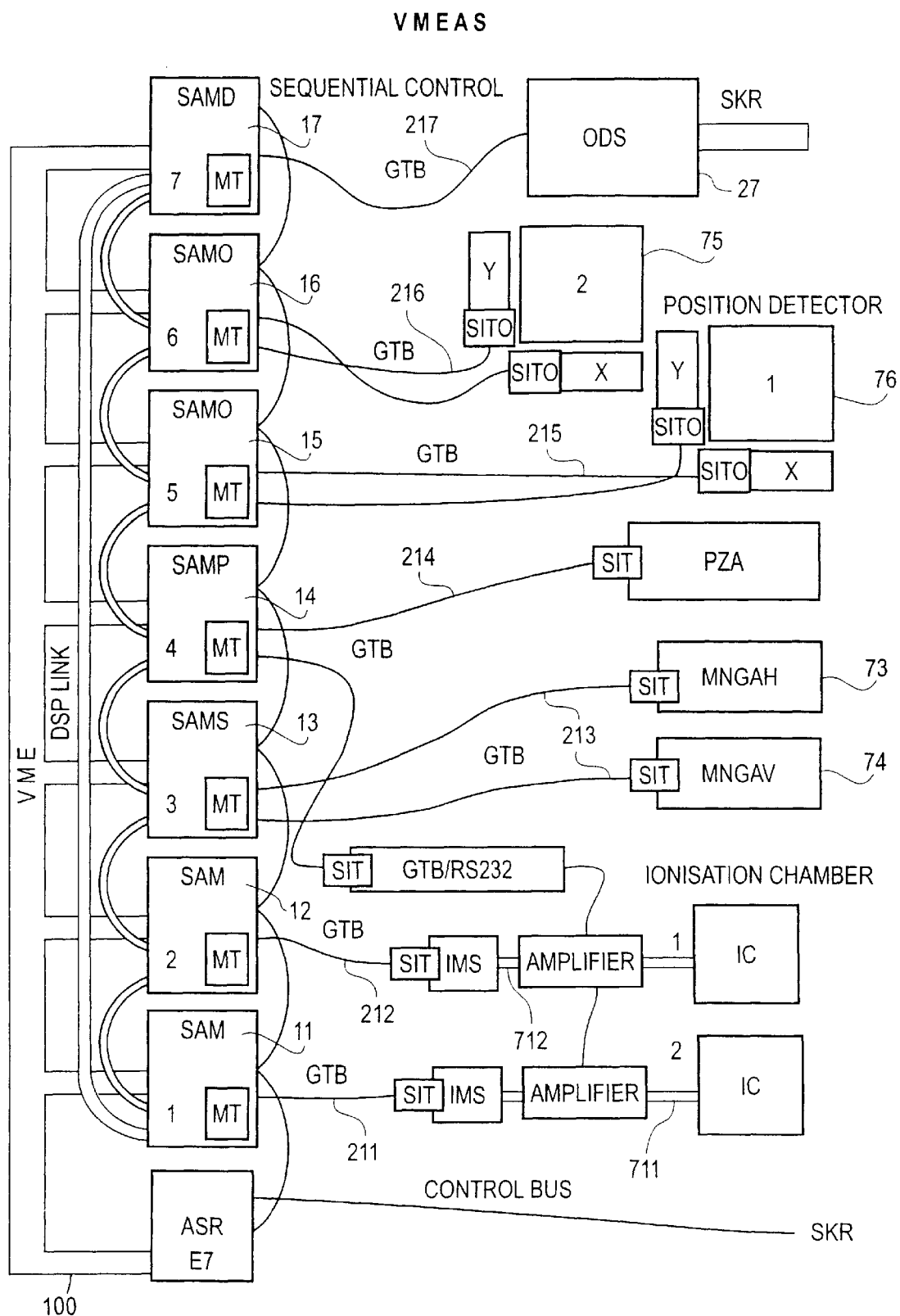

The invention is explained in detail with reference to the drawings, in which:

FIG. 1 is a diagrammatic overview of a heavy ion radiation therapy system in accordance with an exemplary embodiment of the invention, FIG. 2 is an overview of the hardware of the radiation system shown in FIG. 1, FIG. 3 shows diagrammatically the construction of a circuit module, and FIG. 4 shows the connection of the circuit modules with one another and with associated measuring devices.

FIG. 1 gives a diagrammatic overview of a heavy ion radiation therapy system in accordance with an exemplary embodiment of the invention. FIG. 2 gives an overview of the hardware of the radiation system shown in FIG. 1. The ion beam 1, generated in a synchroton, not shown, which has a pulse control centre P, passes on its way to the target volume—the tumour tissue—first of all through a device for monitoring the beam geometry, before it is deflected by x/y deflection units 2 onto a specific point. Before the beam enters the tissue, it passes through a device 3 for monitoring the beam position and the beam width, and through a device 4 for monitoring the beam intensity. Electromagnets are used as the deflecting units. Alternatively, the device 4 can be arranged before the X/Y deflecting units.

Control and monitoring of the radiation system are ensured by a complex electronic system.

The control and monitoring system comprises three levels, namely, a sequential control 5, a system control 6 and an operator prompt facility 7.

These operate independently of one another. Distributed over all three levels is a security system 8, which ensures that the beam is switched off immediately in the event of a malfunction in the system.

The sequential control 5 permits access from the operator prompt facility 7 only during initialisation, during startup and during an emergency stop. During irradiation, the sequential control 5 acts autonomously. Apart from control tasks, it also fulfils security functions, in that the measured data are compared with the specified data for the radiation plan and, in the event of departures above fixed limits, lead to switching off of the beam.

The system control 6 allows the operating parameters, for example, the detector voltages, to be adjusted. In addition, the system control 6 monitors processes running "slowly" by reading out a plurality of system states and, if appropriate, switches off the beam.

The operator prompt facility 7 allows the operator to interact with the control and monitoring system. From here, radiation plans are loaded into the sequential control, 5, radiations are started, stopped or interrupted, operator actions and system parameters are logged, the radiation process and the system status are visually displayed using the measuring data and the measured data are filed for documentation purposes.

The control and monitoring system is in the form of a VME environment and comprises operating devices such as input/output equipment (terminals) and a computing system, consisting of several individual computers, with the customary peripheral devices. The devices for monitoring the beam in respect of location, width and intensity, and also the devices for calling up and deflecting the beam, are coupled to the VME environment via bus connections.

The security system operating independently of the sequential control 5 monitors the radiation process throughout the entire duration of the irradiation. It interrupts the radiation process automatically if deflection of the beam is defective because of a malfunction, or if the particle number for a point, for a slice, or the total particle number applied is exceeded. In this case, the reason for a malfunction can lie in the beam generation or have its origins in the sequential control 5, although the sequential control 5 does itself have control means for interrupting the radiation process.

The sequential control 5 comprises circuit modules (control and readout modules) 11–17, which are connected by a common bus system 100 to the operator controls. The system bus 100 is in the form of a VME bus. Each of the control modules 11–17 is connected by a separate respective apparatus bus 211–217 to a measuring device (ionisation chamber, multiwire chamber) 111–116, and to an external memory device 27. The apparatus buses 211–217 are independent of the system bus 100.

FIG. 3 shows diagrammatically the construction of a circuit module 11–17. Each circuit module contains a microprocessor DSP, at least one read/write memory MEM 1 and at least one input/output interface P1, P2. Advantageously, each circuit module can therefore operate autonomously and requires no central control.

The radiation device is controlled by means of the circuit modules 11–17.

To achieve enhanced system reliability, the devices for measuring location and particle number with the associated circuit modules are present with redundancy in the sequential control 5. Operational failures through random errors in a measuring device can consequently largely be avoided.

FIG. 4 shows the connections of the circuit modules to one another and to the associated measuring devices. To deflect the beam onto a point, deflecting magnets 2 are provided, see FIG. 2, which act on the beam. Deflection is effected in a plane perpendicular to the propagation direction (horizontal/vertical). The deflecting magnets are supplied with electrical energy from magnet power packs 73, 74. The deflecting magnets are activated by the circuit module 13 of the sequential control 5. The circuit module 13 and the deflecting magnets 2 are connected to one another by an apparatus bus. Deflection of the beam is unambiguously defined by 10 current values for activating the two deflecting magnets 2.

To measure the actual deflection of the beam, two position detectors 3 arranged in the path of the beam are provided. The position detectors each comprise a gas-filled multi-wire chamber which records the location of the beam as it passes through and the width of the beam by collecting charges at contacted grids and processing them further electronically. The through-location of the beam is converted by means of the electronics 75, 76 arranged at the chambers into an electrical signal, which is transferred to the circuit module 15, 16 respectively via an apparatus bus. The actual beam location is ascertained at regular time intervals and compared with the desired value in accordance with the radiation plan. These intervals are adjustable as desired; they have a typical value of 150 $\mu$sec.

It is an advantage that the actual beam location and the actual beam width can therefore be continuously monitored. It is then possible to switch off the beam immediately in the event of inconsistency with a desired value.

To determine the particle number delivered by the beam, two ionisation chambers 4 arranged in the path of the beam are provided. The two ionisation chambers are identical. Each ionisation chamber delivers a current signal, the amplitude of which is a measure of the ions that have just passed through, to a downstream current/voltage amplifier 711, 712. The voltage signal that emerges there is scanned at intervals of 12.8 $\mu$sec and converted into a digital value. To determine the beam intensity by means of the microprocessor—a digital signal processor—, the digital values are added up in the circuit module 11, 12 respectively.

The particle number can therefore advantageously be measured at short intervals and response to any overdose harmful to the patient can be immediate.

The sequential control 5 operates on the basis of a data record, which contains all parameters necessary for the radiation process in accordance with the radiation plan. This record includes in particular the points to be irradiated and the particle numbers associated with these points, together with limit values. The points are defined here by the current values for activating the deflecting magnets of the beam guidance system, whilst the associated particle numbers arise from the durations of deflection of the beam onto the particular point.

Continuing with reference to FIG. 4, the method by which the individual circuit modules 11–17 communicate will now be described. In the initialisation phase, the data record for control and monitoring of the therapeutic irradiation of a patient is sent to each of the circuit modules 11–17 by the system bus 100 and is filed there in the memory of each of the circuit modules 11–17. Each circuit module 11–17 therefore possesses the same data record. After the initialisation phase, the system bus connection to the circuit modules 11–17 is interrupted, that is, during the radiation process the circuit modules 11–17 operate autonomously and uninfluenced by the remaining sequential control. This has the advantage that the possibility that a failure in the remaining sequential control will affect the circuit modules 11–17 is excluded.

The radiation process is controlled by sequential execution of the radiation plan point by point by the circuit modules 11–17 of the sequential control 5 in accordance with the raster scan method.

For execution of a point i, the first circuit module 11, which monitors the particle number, reads out the parameter or parameters (for example, the desired particle number)

from the data record filed in its memory and measures the particle number of the beam directed onto this point i. As soon as the desired particle number for the point i has been reached, a trigger signal is set on the trigger bus by the circuit module 11, which causes the circuit modules 11–16 to read out from their memories the parameters they each require for the next point i+1. At the same time, the circuit module 11 sends all parameters for this next point i+1 via a processor interface to the following circuit module 12, setting the measured particle number in the place of the relevant parameter. The following circuit module 12 compares the parameter or parameters read out of its memory, which it requires to execute the point i+1 (for example, again a desired particle number), with the parameter or parameters received from the preceding circuit module, and files all received parameters in its memory in place of the parameters for the relevant point i+1. If the compared parameters are consistent, it can be assumed that the memory content of the circuit module 12 was correct for the relevant point i+1, and the circuit module 12 is operating with the correct parameters. If the two compared parameters are inconsistent, then the following circuit module 12 passes on its parameters for the next point, but an error message is generated, with the result that the radiation is immediately interrupted.

This sequence continues logically for all circuit modules 12 to the circuit module 17 at the top end of the chain.

A readout circuit module 17 is arranged at the top end of the circuit module chain, which awaits receipt of the parameters from its preceding circuit module 16.

These parameters now no longer contain the desired parameter values, but the values measured by the individual circuit modules for the point i. This data record is transmitted from the circuit module 17 via an apparatus bus to an external memory device 27 for filing.

At the same time, this data record is returned via a separate bus connection to the first circuit module 11.

The sequence for the point i+1 now continues as described above for the point i.

If the data record does not arrive within the time needed for the particle number according to the radiation plan, then it can be assumed that at least one of the transmitted parameters of the point i+1 within the chain of the circuit modules 11–17 is inconsistent. If the data record arrives at the circuit module 11 after it has already registered the total particle number for the point i, and hence the point i+1 is already being irradiated, synchronisation is lost. In that case, the circuit module 11 issues an error message, with the result that the radiation process is interrupted.

In the sequential control 5, several functions are therefore advantageously fulfilled at the same time:

All circuit modules contain the same data record, that is, the circuit modules operate consistently.

All circuit modules process the same point, that is, they operate synchronously with one another.

Comparison of data monitors whether there are memory errors in the individual circuit modules.

By overwriting a parameter with a measured value as the parameters are being transmitted, it is possible to collect and read out measured values during the radiation process.

The external memory device 27 is connected to the control and monitoring computer 28 with the other components of the system control by way of the system bus. The progress of the irradiation can be visually displayed at the control and monitoring computer 28. This allows the operator, for instance, the doctor carrying out the treatment, to follow the progress of the irradiation and to interrupt it manually.

The security system operating independently of the sequential control 5 ensures additional monitoring of the radiation process. Additional monitoring of the particle number for each point is essential in this case. For that purpose, a third ionisation chamber is provided, which is identical in arrangement and function with the other two ionisation chambers 4. By means of this third ionisation chamber, apart from the instantaneous particle number (for a point) also the total amount for respectively one plane and all planes is determined. For that purpose, for each irradiated point the charge is collected from the ionisation chamber 4, converted into a pulse sequence and added up in a counter. The instantaneous counter reading is constantly compared with the highest permissible value for the relevant plane. If the desired value is exceeded, then an error message is generated and the radiation process is broken off. Similarly, in a further counter the total particle number, that is, the sum of the particle numbers over all planes, is formed. Here too, to avoid an overdose, comparison with the highest permissible total value is continuous.

What is claimed is:

1. An apparatus for controlling a radiation device, comprising:
   a plurality of circuit modules, each of which includes a memory and a processor, wherein each of the circuit modules is communicatively coupled to two other ones of the circuit modules via respective first and second communication links, and wherein the circuit modules are adapted to use their respective processors to autonomously control the radiation device according to a radiation plan stored in the memories of the circuit modules and to monitor synchronization of the circuit modules via the first and second communication links.

2. The apparatus of claim 1, wherein a first one of the circuit modules is operatively coupled to a radiation beam deflection device, and wherein a second one of the circuit modules is operatively coupled to a radiation intensity measurement device.

3. The apparatus of claim 1, wherein one of the circuit modules is communicatively coupled to an external memory.

4. The apparatus of claim 1, further including a trigger bus to which each of the circuit modules is operatively coupled.

5. The apparatus of claim 1, wherein two of the circuit modules function as a redundant pair of circuit modules.

6. The apparatus of claim 1, wherein each of the circuit modules is adapted to operate autonomously.

7. The apparatus of claim 1, wherein the first and second communication links are data busses.

8. The apparatus of claim 1, wherein the radiation device is a heavy ion radiation device.

9. A method of controlling a radiation device, comprising:
   storing a data record associated with a radiation plan in each of a plurality of circuit modules;
   initiating autonomous execution of the radiation plan by the circuit modules;
   determining within a first one of the circuit modules that a point of the radiation plan has been carried out;
   sending a synchronization signal from the first one of the circuit modules to the other circuit modules in response to the determination that the point of the radiation plan has been carried out; and
   determining within each of the circuit modules a set of parameters associated with a subsequent point of the radiation plan in response to the synchronization signal.

10. The method of claim 9, further including sending the set of parameters determined within the first one of the circuit modules for the subsequent point of the radiation plan from the first one of the circuit modules to a second one of the circuit modules and comparing the set of parameters received from the first one of the circuit modules to the set of parameters determined by the second one of the circuit modules.

11. The method of claim 10, further including generating an error message if the comparison of the sets of parameters indicates an inconsistency between the sets of parameters.

12. The method of claim 11, further including interrupting execution of the radiation plan in response to the error message.

13. The method of claim 9, further including sending measurement data for at least one of the parameters associated with the point of the radiation plan from the first one of the circuit modules to another one of the circuit modules.

14. The method of claim 9, wherein determining within the first one of the circuit modules that the point of the radiation plan has been carried out includes determining that a predetermined amount of radiation has been provided.

15. The method of claim 9, wherein sending the synchronization signal from the first one of the circuit modules to the other circuit modules in response to the determination that the point of the radiation plan has been carried out includes sending the synchronization signal to the other circuit modules via a trigger bus.

16. The method of claim 9, further including
determining within a second one of the circuit modules that one of a radiation beam position and a radiation beam intensity is consistent with the point of the radiation plan at substantially the same time at which the first one of the circuit modules is determining that the point of the radiation plan has been carried out.

17. The method of claim 9, further including using a second one of the circuit modules to control one of a radiation beam position and a radiation beam intensity based on parameter information received from a third one of the circuit modules.

* * * * *